(12) United States Patent
Alt (10) Patent No.: US 7,452,532 B2
(45) Date of Patent: *Nov. 18, 2008

(54) TRANSLUMINAL APPLICATION OF ADULT STEM CELLS FOR BODY ORGAN TISSUE REPAIR

(75) Inventor: Eckhard Alt, Ottobrunn (DE)

(73) Assignee: SciCoTec GmbH, Gruenwald (DE)

( * ) Notice: Subject to any disclaimer, the term of this patent is extended or adjusted under 35 U.S.C. 154(b) by 230 days.

This patent is subject to a terminal disclaimer.

(21) Appl. No.: 10/955,403

(22) Filed: Sep. 30, 2004

(65) Prior Publication Data

US 2005/0079161 A1 Apr. 14, 2005

Related U.S. Application Data

(63) Continuation-in-part of application No. 09/968,739, filed on Sep. 30, 2001, now Pat. No. 6,805,860.

(51) Int. Cl.
*C12N 5/00* (2006.01)

(52) U.S. Cl. ............... 424/93.7; 604/508; 604/509; 604/510; 604/522; 4/325

(58) Field of Classification Search ............. None
See application file for complete search history.

(56) References Cited

OTHER PUBLICATIONS

Barbash et al., "Systematic Delivery of Bone Marrow-Derived from Mesenchymal Stem Cells etc.," Circulation, 108:863-68, 2003.
Orlic et al., "Bone Marrow Cells Regenerate Infracted Myocardium," Letter to Nature, undated.
Sussman, "Heart and Bones," Letters to Nature 410:640-641, 2001.
Rangappa et al., "Transformation of Adult Mesenchymal Stem Cells Isolated from the Fatty Tissue etc.," Ann Thorac. Surg. 75:775-79, 2003.
National Institutes of Health (NIH), "Rebuilding the Nervous System with Stem Cells," NIH web page (http://stemcells.nih.gov).
NIH, "Bone Marrow Stem Cells Useful," 2003.
Study re "Stem Cells Hold Promise for Treating Disease," Journal of Tissue Engineering, Jan. 26, 2002.
Blau et al., "The Evolving Concept of a Stem Cell: Entity or Function?," Cell 105:829-41, Jun. 29, 2001.
"Pancreas Islet Cells can be Injected Through the Hepatic Vein of the Liver," article from Internal Medicine News, Jul. 1, 2003.
Bonner-Weir et al., Pancreatic Stem Cells, J Pathol, 107:519-26, 2002.
Reubinoff B et al., "Neural Progenitors from Human Embryonic Stem Cells," Nature Biotechnology, 19:1134-40, 2001.
Kopen G et al., "Marrow Stromal Cells Migrate Throughout Forebrain and Cerebellum, and they Differentiate into Astrocytes After Injection into Neonatal Mouse Brains," Proc. Natl. Acad. Sci. USA. 96:10711-16, 1999.
Abraham A et al., "Human Pancreatic Islet-Derived Progenitor Cell Engraftment in Immunocompetent Mice," American Journal of Pathology, 164:817-30, 2004.
Masuya M et al., "Hematopoietic Origin of Glomerular Mesangial Cells" Blood, 101, 6:2215-18, 2003.
Rosenthal N, "Prometheus's Vulture and the Stem-Cell Promise" N. Engl. J. Med. 349:267-74, 2003.
Kinnaird T et al., "Local Delivery of Marrow-Derived Stromal Cells Augments Collateral Perfusion Through Paracrine Mechanisms Circulation," 109:1543-49, 2004.
Stedman's Medical Dictionary, 27th Edition, duct, 2003.
Olanow, "Surgical Therapy for Parkinson's Disease," Eur. J. Neurol. 9, 3:31-39, 2002.
Ostenfeld et al., "Recent Advances in Stem Cell Neurobiology," Advances and Technical Standards in Neurosurgery, 28:3-89, 2003.
Anglani et al., "In Search of Renal Stem Cells," G. Ital. Nefrol 19, 6:607-616, 2002.
Gompe, "Liver Repopulation for the Treatment of Metabolic Diseases," J. Inherited Metabolic Disease 24, 2:231-44, 2001.
Schomig A. et al., "Coronary stenting plus platelet glycoprotein IIb/IIIa blockade compared with tissue plasminogen activator in acute myocardial infarction," N Engl J Med 2000; 343:385-391.
Braunwald E. et al., "Myocardial reperfusion, limitation of infarct size, reduction of left ventricular dysfunction, and improved survival: should the paradigm be expanded?," Circulation 1989; 79:441-4.
Goldstein M. A. et al., "DNA synthesis and mitosis in well-differentiated mammalian cardiocytes," Science 1974; 183:212-3.

(Continued)

*Primary Examiner*—Lora E Barnhart
(74) *Attorney, Agent, or Firm*—Hanley, Flight & Zimmerman, LLC (57) ABSTRACT

A method for repairing tissue of a selected organ from among heart, brain, liver, pancreas, kidney, glands, and muscles in a patient's body. Adult stem cells that have the capability to repair tissue of the selected organ are recovered by harvesting from the patient's body. The harvested stem cells are then intraluminally applied through a designated natural body vessel. During the time the stem cells are being applied to the targeted tissue downstream, the designated vessel or duct is selectively occluded to increase concentration and pressure of the applied adult stem cells by the vessel.

11 Claims, 3 Drawing Sheets

OTHER PUBLICATIONS

Claycomb W. C. et al., "Culture of the terminally differentiated adult cardiac muscle cell: A light and scanning electron microscope study," Dev Biol 1980;80:466-482.

Delcarpio J. B. et al., "Morphological characterization of cardiomyocytes isolated from a trans-plantable cardiac tumor derived from transgenic mouse atria (AT-1 cells)," Circ Res 1991:69(6):1591-1600.

Lanson Jr. N. A. et al., "Gene expression and atrial natriuretic factor processing and secretion in cultured AT-1 cardiac myocytes," Circulation 1992; 85(5):1835-1841.

Kline R. P. et al., "Spontaneous activity in transgenic mouse heart: Comparison of primary atrial tumor with cultured AT-1 atrial myocytes," J Cardiovasc Electrophysiol 1993; 4(6):642-660.

Borisov A. B. et al., "Proliferative potential and differentiated characteristics of cultured cardiac muscle cells expressing the SV 40 T oncogene," Card Growth Reg 1995; 752:80-91.

Claycomb W. C. et al., "HL-1 cells: A cardiac muscle cell line that contracts and retains phenotypic characteristics of the adult cardiomyocyte," Proc Natl Acad Sci USA 1998; 95:2979-84.

Watanabe E. et al., "Cardiomyocyte transplantation in a porcine myocardial infarction model," Cell Transplant 1998; 7(3):239-246.

Watanabe E. et al., "Effect of basic fibroblast growth factor on angiogenesis in the infarcted porcine heart," Basic Res Cardiol 1998; 93:30-7.

Lee J. S. et al., "Gene therapy for therapeutic myocardial angiogenesis: A promising synthesis of two emerging technologies," Nat Med 1998; 4(6):739-42.

Kocher A. A. et al., "Neovascularization of ischemic myocardium by human bone-marrow-derived angioblasts prevents cardiomyocyte apoptosis, reduces re-modeling and improves cardiac function," Nat Med 2001; 7(4)430-6.

Taylor D. A. et al., "Regenerating functional myocardium: Improved performance after skeletal myoblast transplantation," Nat Med 1998; 4(8):929-33.

Scorsin M. et al., "Comparison of the effects of fetal cardiomyocyte and skeletal myoblast transplantation on postinfarction left ventricular funtion," J Thorac Cardiovasc Surg 2000; 119:1169-75.

Galli R et al., "Skeletal myogenic potential of human and mouse neural stem cell," Nat Neurosci 2000;3:986-991.

Jackson K. A. et al., "Regeneration of ischemic cardiac muscle and vascular endothelium by adult stem cells," J Clin Invest 2001;107(11):11395-402.

Prockop D. J. et al., "Marrow stromal cells for non hematopoetic stem tissues," Science 1997; 276:71-74.

Orlic D. et al., "Bone marrow cells regenerate infarcted myocardium," Nature 2001; 410:701-5.

Zuk P. A. et al., "Multilineage cells from human adipose tissue: Implications for cell-based therapies," Tiss Engin 2001; 7(2):211-28.

Kehat I. et al., "Human embryonic stem cells can differentiate into myocytes with structural and functional properties of cardiomyocytes," J Clin Invest 2001; 108:407-14.

Klug M. G. et al., "Genetically selected cardiomyocytes from differentiating embryonic stem cells form stable intracardiac grafts," J Clin Invest 1996; 98(1):216-24.

Thomson J. A. et al., "Isolation of a primate embryonic stem cell," Proc Natl. Acad Sci USA 1995; 92:7844-48.

Makino S. et al., "Cardiomyocytes can be generated from marrow stromal cells in vitro," J Clin Invest 1999; 103:697-705.

TRANSLUMINAL APPLICATION OF ADULT STEM CELLS FOR BODY ORGAN TISSUE REPAIR

CROSS-REFERENCE TO RELATED APPLICATION

This application is a continuation-in-part of Ser. No. 09/968,739, filed Sep. 30, 2001, now U.S. Pat. No. 6,805,860, of the same applicant. Applicant claims priority of the '739 application with respect to common subject matter.

BACKGROUND OF THE INVENTION

The present invention relates generally to transluminal application of therapeutic cells for tissue repair, such as myocardial repair, and more particularly to balloon catheter protected transluminal application of multipotent cells for repair of a failing body organ such as heart, brain, liver, kidney or pancreas, and even related glands, nerves, and muscles. It is a principal aim of the invention to provide a novel method to repair failing tissue.

In principle, the human body has three types of cells. One type constitutes cells that continuously undergo replication and reproduction, such as dermal cells and epithelial cells of the intestine, for example. These cells, which have a life as short as ten days, are replaced by the same cell type which is replicating continuously. A second type of cell is differentiated in the adult state, but has the potential to undergo replication and the ability to reenter the cell cycle under certain conditions, an example being liver cells. The liver has the capacity to regrow and repair itself even if a tumor is excised and a major portion of the liver is removed. The third cell type comprises those cells that stop dividing after they have reached their adult stage, such as neuro cells and myocardial cells.

For the latter type or group of cells, the number of cells in the body is determined shortly after birth. For example, myocardial cells stop dividing at about day ten after delivery, and for the rest of its life the human body has a fixed number of myocardial cells. Changes in myocardial function occur not by division and new cell growth, but only as a result of hypertrophy of the cells.

Although the absence of cell division in myocardial cells is beneficial to prevent the occurrence of tumors—which practically never occur in the heart—it is detrimental with regard to local repair capacities. During the individual's lifetime, myocardial cells are subjected to various causes of damage, that irreversibly lead to cell necrosis or apoptosis.

The primary reason for cell death in the myocardium is ischemic heart disease—in which the blood supply to the constantly beating heart is compromised through either arteriosclerotic build-up or acute occlusion of a vessel following a thrombus formation, generally characterized as myocardial infarction (MI). The ischemic tolerance of myocardial cells following the shut-off of the blood supply is in a range of three to six hours. After this time the overwhelming majority of cells undergoes cell death and is replaced by scar tissue.

Myocardial ischemia or infarction leads to irreversible loss of functional cardiac tissue with possible deterioration of pump function and death of the individual. It remains the leading cause of death in civilized countries. Occlusion of a coronary vessel leads to interruption of the blood supply of the dependent capillary system. After some 3 to 6 hours without nutrition and oxygen, cardiomyocytes die and undergo necrosis. An inflammation of the surrounding tissue occurs with invasion of inflammatory cells and phagocytosis of cell debris. A fibrotic scarring occurs, and the former contribution of this part of the heart to the contractile force is lost. The only way for the cardiac muscle to compensate for this kind of tissue loss is hypertrophy of the remaining cardiomyocytes (accumulation of cellular protein and contractile elements inside the cell), since the ability to replace dead heart tissue by means of hyperplasia (cell division of cardiomyocytes with formation of new cells) is lost shortly after the birth of mammals.

Other means of myocardial cell alteration are the so-called cardiomyopathies, which represent various different influences of damage to myocardial cells. Endocrine, metabolic (alcohol) or infectious (virus myocarditis) agents lead to cell death, with a consequently reduced myocardial function. The group of patients that suffer myocardial damage following cytostatic treatment for cancers such as breast or gastrointestinal or bone marrow cancers is increasing as well, attributable to cell necrosis and apoptosis from the cytostatic agents.

Heretofore, the only means for repair has been to provide an optimal perfusion through the coronary arteries using either interventional cardiology—such as PTCA (percutaneous transluminal coronary angioplasty), balloon angioplasty or stent implantation—or surgical revascularization with bypass operation. Stunned and hibernating myocardial cells, i.e., cells that survive on a low energy level but are not contributing to the myocardial pumping function, may recover. But for those cells which are already dead, no recovery has been achieved.

The current state of interventional cardiology is one of high standard. Progress in balloon material guide wires, guiding catheters and the interventional cardiologist's experience as well as the use of concomitant medication such as inhibition of platelet function, has greatly improved the everyday practice of cardiology. Nevertheless, an acute myocardial infarction remains an event that, even with optimal treatment today, leads to a loss of from 25 to 100% of the area at risk—i.e., the myocardium dependent on blood supply via the vessel that is blocked by an acute thrombus formation. A complete re-canalization by interventional means is feasible, but the ischemic tolerance of the myocardium is the limiting factor.

A recent article published in the New England Journal of Medicine (Schomig A. et al., "Coronary stenting plus platelet glycoprotein IIb/IIIa blockade compared with tissue plasminogen activator in acute myocardial infarction," *N Engl J Med* 2000; 343:385-391), for which the applicant herein was a clinical investigator, reports on a study of the myocardial salvage following re-canalization in patients with an acute myocardial infarction. The average time until admission to the hospital in these patients was 2.5 hours and complete re-canalization was feasible after 215 minutes, roughly 3.5 hours. Nevertheless, only 57% of the myocardium at risk could be salvaged by re-canalization through interventional cardiology by means of a balloon and stent. When the group of patients was randomized to the classical thrombolytic therapy, which is the worldwide standard (with no interventional means), only 26% of the myocardium at risk could be salvaged. This means that even under optimal circumstances more than 40% of the myocardial cells are irreversibly lost.

With the knowledge that many patients arrive at a hospital at from 6 to 72 hours after the acute symptoms of vessel blockage by a thrombus, one can assume that the average loss of affected myocardial tissue is in a range of from 75 to 90% following an acute MI.

As noted above, cells can survive on a lower energy level, referred to as hibernating and stunning myocardium. As the collateral blood flow increases or re-canalization provides new blood supply they can recover their contractile function.

The principle of myocardial re-perfusion, limitation of infarct size, reduction of left ventricular dysfunction and their effect on survival were described by Braunwald (Braunwald E. et al., "Myocardial reperfusion, limitation of infarct size, reduction of left ventricular dysfunction, and improved survival: should the paradigm be expanded?," *Circulation* 1989; 79:441-4).

Annually, about five million Americans survive an acute myocardial infarction. Clearly then, loss of affected myocardial tissue is a problem of major clinical importance. Currently, repair is limited to hypertrophy of the remaining myocardium, and optimal medical treatment by a reduction in pre- and after-load as well as the optimal treatment of the ischemic balance by β-blockers, nitrates, calcium antagonist, and ACE inhibitors.

If it were feasible to replace the dead myocardium (scar tissue) by regrowing cells, such a technique would have a profound impact on the quality of life of affected patients.

As noted earlier herein, in addition to ischemic heart disease other reasons exist for the reduction of myocardial cells that contribute to the pumping or electrical function of the heart. Among them are the cardiomyopathies, which describe a certain dysfunction of the heart. Reasons are many, such as chronic hypertension which ultimately leads to a loss in effective pumping cells, and chronic toxic noxious such as alcohol abuse or myocarditis primarily following a viral infection. Also, cell damage in conjunction with cytostatic drug treatment is becoming of greater clinical relevance. Not only the contracting myocardium becomes effected, but also the so called conduction system of the heart. Clinical symptoms are slow or too fast heart rates, generally called sinus node disease, AV Block conduction block and re-entry tachycardias and atrial flutter, atrial fibrillation, ventricular tachycardias and ventricular fibrillation.

The group of William C. Claycomb et al. has been engaged in research on the behavior and the development of myocytes since the early 1970's. In their initial report (Goldstein M. A. et al., "DNA synthesis and mitosis in well-differentiated mammalian cardiocytes," *Science* 1974; 183:212-3), they described the incorporation of 3H-Thymidin into the nuclei of heart cells of two days old rats which indicates that neonatal cardiac cells still undergo synthesis of DNA and divide despite the presence of contractile proteins. This phenomenon of cell division ceases at day 17 of the postnatal development. After that time no further division of cardiac cells occurs, either in rats or in humans.

The interest in mammalian cardiomyocytes has led to the development of cultures of adult cardiac muscle cells (Claycomb W. C. et al., "Culture of the terminally differentiated adult cardiac muscle cell: A light and scanning electron microscope study," *Dev Biol* 1980;80:466-482), and ultimately to the generation of a transplantable cardiac tumor-derived transgenic AT1-cell.

During the 1980's intensive studies were conducted with the characterization of this atrial derived myocyte cell line, which is immortalized by the introduction of the SV40-large-T-oncogene (SV40-T). From this AT-1-cell-group, other adult cardiomyocytes have been derived. These can be passaged indefinitely in culture, can be recovered from a frozen stock, can retain a differentiated cardiomyocyte phenotype, and maintain their contractile activity. They are described as HL-1-cells. The reader is referred, for example, to Delcarpio J. B. et al., "Morphological characterization of cardiomyocytes isolated from a trans-plantable cardiac tumor derived from transgenic mouse atria (AT-1 cells)," *Circ Res* 1991; 69(6):1591-1600; Lanson Jr. N. A. et al., "Gene expression and atrial natriuretic factor processing and secretion in cultured AT-1 cardiac myocytes," *Circulation* 1992; 85(5):1835-1841; Kline R. P. et al., "Spontaneous activity in transgenic mouse heart: Comparison of primary atrial tumor with cultured AT-1 atrial myocytes," *J Cardiovasc Electrophysiol* 1993; 4(6):642-660; Borisov A. B. et al., "Proliferative potential and differentiated characteristics of cultured cardiac muscle cells expressing the SV 40 T oncogene," *Card Growth Reg* 1995; 752:80-91; and Claycomb W. C. et al., "HL-1 cells: A cardiac muscle cell line that contracts and retains phenotypic characteristics of the adult cardiomyocyte," *Proc Natl Acad Sci USA* 1998; 95:2979-84.

Finally, the cardiomyocyte transplantation in a porcine myocardial infarction model has been studied intensively in collaboration with the research group of Frank Smart (Watanabe E. et al., "Cardiomyocyte transplantation in a porcine myocardial infarction model," *Cell Transplant* 1998; 7(3): 239-246). In conjunction with the AT-1 cardiomyocytes, human fetal cardiomyocytes were injected through a syringe and needle into the adult pig heart infarction area.

In summary, these cells showed local growth and survived in the infarction border zone, but could not be found in the core scar tissue of the myocardial infarction. The majority of the implanted cells were replaced with inflammatory cells, suggesting that the immuno-suppressant regimen that was concomitantly applied was not sufficient for the grafted cells to survive in the host myocardium. Other factors that may have influenced the result that the transplanted cells were not detected, could possibly be linked to the fact that the cells were grafted 45 days after inducing the infarction.

It is known that the inflammatory stimuli for cell growth are significantly reduced in the first two to three weeks of an MI. Also, that transforming-growth-factor-β (TGF-β), fibroblast-growth-factor-2 (FGF-2), platelet-derived-growth-factor (PDGF) and other cytokines, like the interleucin-family, tumor-necrosis-factor-a (TNF-a) and interferon-gamma are strong stimulators of cell proliferation and cell growth. The adjunct therapy with immuno-suppression has further reduced this stimuli for cell growth.

Another major factor for the failure of detection of grafted cells in the myocardial scar may be the selection of the infarction model. An artery is occluded and the blood supply has not recovered before grafting. There is no reason to assume that the grafted cells could survive in an ischemic area and grow, better than the myocytes.

Therefore, other groups have tried to induce a myocardial angiogenesis by gene-therapy. This was either performed by the administration by fibroblast growth factor II in the presence or absence of heparin (see Watanabe E. et al., "Effect of basic fibroblast growth factor on angiogenesis in the infarcted porcine heart," *Basic Res Cardiol* 1998; 93:30-7) or by application of vascular endothelial growth factor (VEGF), a potent mitogen for endothelial cells. VEGF stimulates capillary formation and increases vascular permeability (Lee J. S. et al., "Gene therapy for therapeutic myocardial angiogenesis: A promising synthesis of two emerging technologies," *Nat Med* 1998; 4(6):739-42). Still other groups have tried to increase the collateral capillary blood flow by human bone marrow derived angioblasts and have shown an improvement in acute myocardial infarction in rats treated with injections of colony-stimulating-factor-G (CSF-G) mobilized adult human CD-34 cells (Kocher A. A. et al., "Neovascularization of ischemic myocardium by human bone-marrow-derived angioblasts prevents cardiomyocyte apoptosis, reduces re-modeling and improves cardiac function," *Nat Med* 2001; 7(4):430-6).

While these approaches certainly have some research merit, their clinical relevance for the majority of patients is not as important, since we have effective means to re-canalize an occluded vessel and provide a blood supply via the natural branching of the coronary arteries, which further subdivides into arterioles and capillaries.

Other attempts to transplant preformed patches also necessitate the growth of the grafted cells in a patch formation and a surgical operation in a patient, which requires opening the thoracic cage.

Considering the complications, the cost and the risk associated with these time consuming procedures, it becomes clear that they offer only limited likelihood for widespread routine application.

Other groups have tried to make use of the precursor cells that are found in the peripheral muscle. Unlike the heart, there is a certain degree of repair in peripheral skeletal muscles, since the peripheral skeletal muscle contains progenitor cells, which have the capability to divide and replace the peripheral muscle. By isolating those cells from a probe of a thigh muscle, the progenitor cells of skeletal muscle have been separated, cultured and re-injected in an animal model (Taylor D. A. et al., "Regenerating functional myocardium: Improved performance after skeletal myoblast transplantation," *Nat Med* 1998; 4(8):929-33; Scorsin M. et al., "Comparison of the effects of fetal cardiomyocyte and skeletal myoblast transplantation on postinfarction left ventricular function," *J Thorac Cardiovasc Surg* 2000; 119:1169-75), and more recently in some patients also.

The application of these cultured cells has also been attempted by injection with small needles following an opening of the subject's chest and the pericardial sac. While in the model of kryo-infarction, in which only the myocardial cells die but the blood supply through the vascular system is not limited, the injection of autologous skeletal myoblasts improves the myocardial function. The results indicated, however, that the engrafted cells retain skeletal muscle characteristic, which means they cannot contract at the constant fast rate imposed by the surrounding cardiac tissue. In addition, no electrical connection exists between the graft cells and the host tissue, and it is assumed that their contribution to improve contractile performance probably resulted from the mechanical ability of the engrafted contractile tissue to respond to stretch activation by contraction.

Considering the experience with latissimus dorsi muscle grafting—a procedure called dynamic cardiomyoblasty—, the disappointing results with the possible use of skeletal muscle as a myocardial substitute indicate that the long term different muscle characteristics of skeletal muscles do not match the need of a constantly pumping myocardial cell. Therefore, the best these cells might achieve would be to improve the quality of the scar of the ischemic myocardium, but not actively contribute to a contraction of this area in the long term.

SUMMARY OF THE INVENTION

The present invention is directed to interventional medicine through an intraluminal application of cells that have the capability to replace the necrotic tissue of a failing organ, such as the heart in the case of a MI, to resume the myocardial function and therefore improve the pumping performance of the myocardium. The procedure is oriented on the clinical practice of interventional cardiology following the principle that only those approaches that are both (a) relatively easy to perform, with little or no risk to the patient but a potentially high benefit, and (b) highly cost effective, are likely to be routinely applied in everyday medicine.

An important aspect of the invention is that the cells to be used in the intraluminal or transluminal application preferably are autologous adult stem cells, which are derived from the same patient that has suffered the infarction. The cells are harvested and separated before injection, from the same individual (autologous transplantation). In a case of failing tissue of the myocardium, these cells are then injected into the coronary artery that caused the infarction or into the corresponding coronary vein in a retrograde manner.

The approach taken according to the invention recognizes that the stem cells need a certain contact time to adhere and migrate from the vascular bed into the infarcted myocardial area. In contrast to previous approaches, in which patches or applications through needles into the infarcted area have been considered, the approach of the invention hypothesizes that the most effective way to deliver the cells to the infarcted area is through the vascular tree of coronary arteries, arterioles and capillaries that supply the infarcted area. An occlusion balloon of an over the wire type catheter is inflated at the site of the primary infarction, after the vessel has been re-canalized and the blood flow reconstituted.

Importantly, while the blood flow is still blocked, the stem cells are supplied by slow application through the balloon catheter over a relatively short period of time, on the order of 1 to 15 minutes, for example. That is, the stem cells are injected through the inner lumen of the catheter while the balloon is inflated, and therefore, no washout occurs. It is believed by applicant that this intracoronary, intravascular, intraluminal, or transcoronary application of cells during a period that flow or perfusion is ceased is critical to enabling the cells to successfully attach to the vessel or myocardial wall. And further, to overcome more actively the endothelial barrier following the increased pressure in the vascular bed or duct, which is attributable to the retrograde flow of cells being limited through the inflated balloon catheter.

The principles of the invention are not limited to cellular repair of damaged or failing myocardial tissue, but may be applied in processes for repair of tissue of various organs of the body, additionally including the brain, liver, kidney, pancreas, lungs, related glands, nerves, and muscles, for example, by intraluminal application of the stem cells through an appropriately designated vessel or duct leading to the targeted tissue.

Thus, according to the invention, a method for repairing tissue of an organ in a patient's body includes delivering adult stem cells that have the capability to replace tissue of a failing organ to the site of the tissue to be repaired, by an intraluminal application through a blood vessel of the site, and occluding the blood vessel proximal to the location of cell entry therein via the intraluminal application during at least a portion of the duration of the cell delivery to increase the concentration of cells delivered to the site. The intraluminal application of adult stem cells through a blood vessel may be performed through an arterial vessel or a venous vessel, according to the target organ. Preferably, a balloon catheter is employed for the intraluminal application, and the occlusion of the blood vessel is performed by inflating the balloon of the catheter for a time interval prescribed to increase the concentration of cells delivered to the site. Initially, a guide wire is introduced through the blood vessel to the site, and thereafter the catheter is advanced over the guide wire until the distal end of the catheter reaches a selected point in the vicinity of the site for delivering the adult stem cells.

The autologous adult cells may be harvested from the patient's own body, such as from the patient's bone marrow, adipose tissue, or may originate from lipoaspirate, as the source of the cells to be delivered to the site. Preferably, the harvesting is performed within a sufficiently short time interval immediately prior to delivery of the cells to the organ site to enhance the likelihood of successful organ tissue repair.

Further according to the invention, a procedure for repairing tissue of an organ in a patient's body comprises delivering adult stem cells that have the capability to replace tissue of a failing organ to the site of the organ tissue to be repaired by intraluminal application through a duct leading to the targeted organ site. The duct is one normally supporting secretion flow from the organ or a related gland. The intraluminal application includes advancing a catheter through the duct to the vicinity of the site, and occluding the duct proximal to the location of the intraluminal application during the cell delivery to enhance the concentration of cells delivered to the site. The intraluminal application may be performed in a retrograde manner though the duct.

Here also, a balloon catheter is used, along with over-the-wire guidance of the distal end of the catheter to the target organ site. Occlusion of the duct is performed by inflating the balloon of the catheter for a time interval prescribed to achieve the enhancement of cell concentration. Harvesting of the stem cells is preferably performed from the patient's own body in the manner indicated above.

Stated somewhat more simply, the method involves delivering adult multipotent cells to a patient's organ through a balloon catheter placed in a vessel or duct supporting the organ by occluding the vessel or duct at least partially and temporarily during cell delivery proximal to the site of cell delivery for enhanced engraftment of the cells applied to the specific organ.

BRIEF DESCRIPTION OF THE DRAWINGS

The above and still further aims, objectives, features, aspects and attendant advantages of the present invention will become apparent to those skilled in the art from the following detailed description of a best mode presently contemplated of practicing the invention by reference to certain preferred methods of application thereof, taken in conjunction with the accompanying figures of drawing, in which.

DETAILED DESCRIPTION OF THE PRESENTLY CONTEMPLATED BEST MODE OF PRACTICING THE INVENTION

In an exemplary process that applies the principles of the present invention to repair of myocardial tissue, the ischemically injured cardiac tissue is subjected to invasion by stem cells, preferably adult stem cells, with subsequent differentiation into beating cardiomyocytes which are mechanically and electrically linked to adjacent healthy host myocardium, thereby resembling newly formed and functionally active myocardium.

Until recently it had been hypothesized by most researchers that adult stem cells are tissue specific. It was thought that a certain stem cell-like population exists in every organ and is capable of differentiation into this certain tissue with exceptions to this rule regarding repair in heart and brain. Relatively recent studies have indicated an underestimated potential of these cells. It has been shown that murine and human neural stem cells (NSC) give rise to skeletal muscle after local injection (see, for example, Galli R et al., "Skeletal myogenic potential of human and mouse neural stem cells," Nat Neurosci 2000;3:986-991). Bone marrow stem cells have also been shown to replace heart tissue (cardiomyocytes, endothelium and vascular smooth muscle cells) after injection into lethally irradiated mice with a myocardial infarction (see Jackson K. A. et al., "Regeneration of ischemic cardiac muscle and vascular endothelium by adult stem cells," J Clin Invest 2001;107(11):11395-402). The tissue damage in general appears to transmit signals which direct multi-potential stem cells to the site of destruction, and these precursors undergo a multi-step process of migration and differentiation at the organ site to replace damaged cells in form and function.

Experiments with cultured fetal cardiac myocytes or neonatal myocytes impose limitations owing to their heterologous nature and their possible induction of an immuno response necessitating an immuno-suppressive therapy. Complications and risks associated with an immuno-suppressant therapy are an increased susceptibility to infection and the possible development of malignancies. In addition, it is speculated that only a few patients would be willing to undergo a long term immuno-suppressive therapy with all its negative side effects.

An alternative approach by Prockop suggests that marrow stromal cells act as stem cells for non hematopoetic tissue and are capable to differentiate into various types of cells including bone, muscle, fat, hyaline cartilage and myocytes (Prockop D. J. et al., "Marrow stromal cells for non hematopoetic stem tissues," Science 1997; 276:71-74).

Some recent findings have stimulated interest in adult cardiomyocytes. A report in Nature describes the ability to inject adult bone marrow stem cells from transgenic mice into the border of infarcted myocardial tissue (Orlic D. et al., "Bone marrow cells regenerate infarcted myocardium," Nature 2001; 410:701-5). According to this report, these adult stem cells are capable of differentiation into cardiomyoblasts, smooth muscle cells and endothelial cells after injection. The infarcted myocardium implied that the transplanted cells responded to signals from the injured myocardium which promoted their migration, proliferation and differentiation within the necrotic area of the ventricular wall.

One is then left to consider the most effective techniques to obtain adult stem cells. The classical way to recover stem cells is a bone marrow tap. The bone marrow contains a wide variety of hematopoetic and mesenchymal stem cells in addition to the T-lymphocytes, macrophages, granulocytes and erythrocytes. By incubation with monoclonal antibodies specific for the respective cell lineages and by sorting and removing with a biomagnet after incubation with magnetic beads and cell sorting with FACS (fluoroscopy activated cell sorting), a highly enriched cell line of bone marrow derived stem cells can be insulated, cultured and grown.

Aside from the classical approach of a bone marrow tap, a recent report states that cells from human adipose tissue contain a large degree of mesenchymal stem cells capable of differentiating into different tissues in the presence of lineage specific induction factors including differentiation into myogenic cells (see Zuk P. A. et al., "Multilineage cells from human adipose tissue: Implications for cell-based therapies," *Tiss Engin* 2001; 7(2):211-28). The interesting approach in this research is that out of a lipoaspirate of 300 cm$^3$ from the subcutaneous tissue, an average of $2-6\times10^8$ cells can be recovered. Even if one assumes that after processing of this liposuction tissue and separation and isolation of the mesenchymal stem cells, only 10% of these stem cells might be left for culture, the remaining approximately $10^7$ (10 million) cells would be quite sufficient to be used for the intraluminal or transluminal transplantation process of the present invention.

A benefit of this latter approach could be that culture and passaging of the stem cells might be avoided. This is of special importance, since in the early phases of myocardial infarction there is a high activity of inflammatory cytokines which promote adhesion, migration and proliferation of the stem cells. In addition, as long as there is no scar core tissue it is much easier for these cells to migrate into the whole area of myocardial infarction and resume the cardiac function.

Recently, embryonic stem cells have been the subject of intensive discussion, particularly their pluripotency to differentiate into a vast range of tissues and organs of the human body that are in need for repair. The discussion has included the potential use of such stem cells for replacement of insulin producing cells as well as embryonic stem cells that can differentiate into cells with structural and functional properties of cardiomyocytes. This is described in the August 2001 issue of the *Journal of Clinical Investigation* (Kehat I. et al., "Human embryonic stem cells can differentiate into myocytes with structural and functional properties of cardiomyocytes," *J Clin Invest* 2001; 108:407-14). Earlier, the proliferation of embryonic stem cells had been very elegantly described in principle by Field and co-workers (Klug M. G. et al., "Genetically selected cardiomyocytes from differentiating embryonic stem cells form stable intracardiac grafts," *J Clin Invest* 1996; 98(1):216-24). In their attempt, the latter group succeeded in plating a cell line following a fusion gene consisting of the a—cardiac-myocyte-heavy-chain-promotor and the c-DNA encoding aminoglycoside-phosphotransferase that was stably transfected into pluripotent embryonic stem cells. The resulting cell lines were differentiated in vitro and subjected to a G418 selection. By this means, the selected cardiomyocyte cultures were 99.6% pure and highly differentiated.

It is important to consider not only the engraftment of pluripotent embryonic stem cells into a failing organ, but also the possibility of resulting tumor formation. Therefore, the pluripotent embryonic stem cells need to be cultured in an undifferentiated status, transfected via electroporation and grown in differentiated cultures. The interesting approach in this work is the high yield of selected embryonic stem cell derived cardiomyocytes which, with simple genetic manipulation, can be used to produce pure cultures of cardiomyocytes. The authors assumed that this elective approach could be applicable to all stem cell derived cell lineages. It has also been reported by others that isolation of primate embryonic stem cells with cardiogenic differentiation is feasible (Thomson J. A. et al., "Isolation of a primate embryonic stem cell," *Proc Natl. Acad Sci USA* 1995; 92:7844-48).

In addition, it was recently reported that human cardiomyocytes can be generated from marrow stromal cells in vitro as well, but with a low yield of differentiated myocytes (Makino S. et al., "Cardiomyocytes can be generated from marrow stromal cells in vitro," *J Clin Invest* 1999; 103:697-705). And as noted above, the 1997 Prockop report in *Science* describes another line of cardiomyocytes generated from marrow stromal cells in vitro. This cardiomyogenic cell line was derived from murine bone marrow stromal cells that were immortalized and treated with 5-azacytidine. By mechanically separating spontaneously beating cells, a cell line was isolated that resembled a structure of fetal ventricular cardiomyocytes expressing iso-forms of contractile protein genes such as alpha cardiomyocyte heavy chain, -light chain, a-actin, Nkx2.5-Csx, GATA-4, tef-1, MEF-2a und MEF-2D.

While these embryonic stem cells provide optimism for the future that cardiomyocytes derived from embryonic cells might fulfill the requirements of cells that can (a) be passaged indefinitely in culture, (b) be recovered from frozen stocks and are readily available if a patient with a myocardial infarction comes to the cath lab, (c) retain their differentiated cardiomyocyte phenotype and (d) maintain contractile activity with minimum or no immunogenity, further basic research is needed on those cells before they can be applied in the animal model. It is likely that a primate model of infarction and the transplantation of primate embryonic stem cell derived cardiomyocytes may be needed as the final proof of principle before a human study might be conducted.

Presently, for ethical, immunological and feasibility reasons the applicant herein submits that transplantation of autologous adult stem cells (derived from the same individual that suffers the infarction) is the most straightforward and practical approach to repair failing myocardium. The process of the invention promotes invasion of ischemically injured cardiac tissue by stem cells that firmly attach and subsequently undergo differentiation into beating cardiomyocytes that are mechanically and electrically linked to adjacent healthy host myocardium. Adhesion of the injected stem cells and their migration beyond the endothelial barrier may be confirmed by observation after several days of frozen sections using light microscopy and, subsequently, electron microscopy. For evidence of the transition of stem cells into cardiomyocytes, markers are introduced into the stem cells before they are re-injected into the myocardial tissue to be repaired.

One approach might be to transplant male cells carrying the Y-chromosome into a female organism, but at least two factors weigh against this. It could lead to immunologic problems because of the different cell surfaces carried by the recipient and the donor (heterologous transplant), a potential reason that some studies are not able to show a successful heterologous cell transplantation. Even more importantly, a predominance of inflammatory cells exists at the site of myocardial injury, which leads to an immediate recognition of foreign cell surface proteins with consequent elimination of the cells. Use of autologous stem cells would not carry this immunologic risk of cell destruction, although some difficulty is encountered in prior introduction of genetic or protein markers into those cells.

To overcome this difficulty, a green fluorescence protein (GFP) is used as a marker, with introduction into the stem cell genome by liposomal gene transfer. Cells can then be identified after transplantation by fluorescence microscopy. As part of the procedure, stem cells are also marked by 3H-Thymidin, a radioactive labeled part of DNA. All stem cells undergoing DNA replication for mitosis will introduce 3H-Thymidin into their genome, and thus can be detected afterwards by gamma count. One limitation of this process is the fact that radioactivity (per volume) declines with each subsequent cell division (albeit initial total radioactivity stays constant). Nevertheless, this marker aids in developing a gross estimate of the amount of cells in a certain organ or tissue (e.g., heart, spleen, liver etc.).

Reference will now be made to the accompanying Figures of drawing in describing an exemplary process. It should be noted at the outset that the Figures are not intended to be to scale, nor to do more than serve as a visual aid to the description. In those Figures representing the human body or body parts, certain components may be exaggerated relative to others for the sake of emphasis or clarity of the respective accompanying description. The autologous adult stem cells (more broadly, multipotent cells) are harvested in one of the known ways generally described above, such as by bone marrow tap or from adipose tissue, for processing and possible cultivation.

Figure 1:
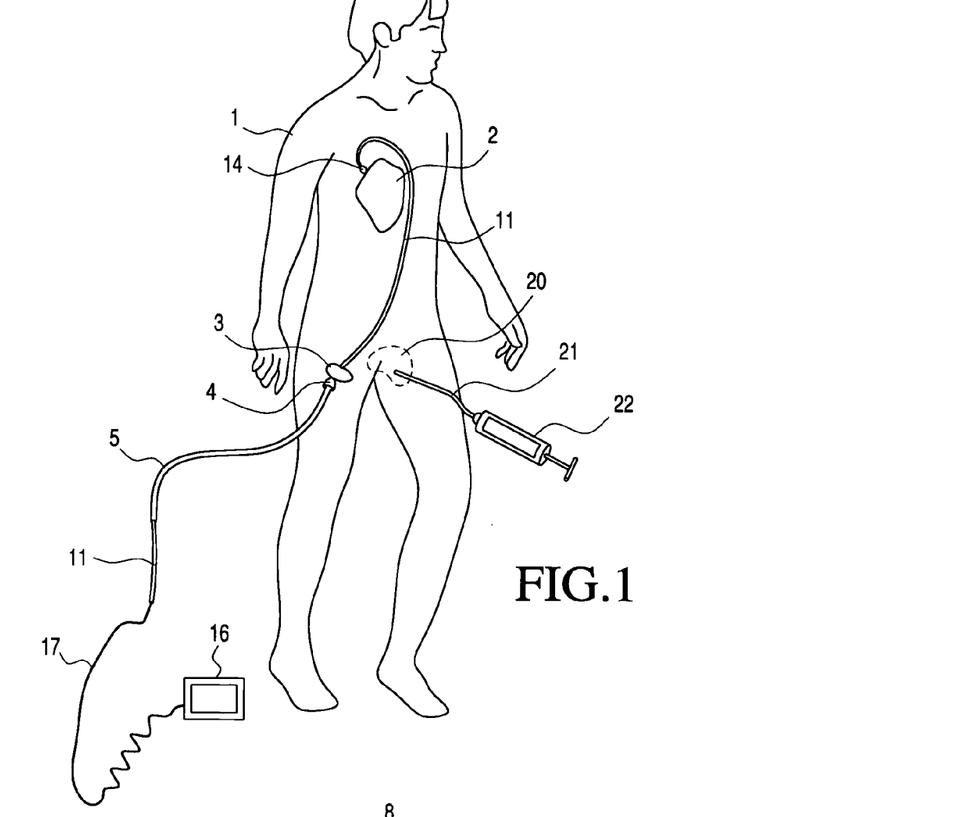
FIG. 1 is a transparent front view of a patient showing exemplary locations of obtaining autologous adult stem cells from the patient, and of injecting the harvested stem cells into the cardiovascular system and through a balloon catheter for introduction at the site of myocardial tissue damage to be repaired.

In an exemplary technique, and referring to FIG. 1, subcutaneous adipose tissue 20 is obtained from a liposuction procedure on the patient 1 during local anesthesia. In this procedure, a hollow canule or needle 21 is introduced into the subcutaneous space through a small (approximately 1 cm) cut. By attaching gentle suction by a syringe 22 and moving the canule through the adipose compartment, fat tissue is mechanically disrupted and following the solution of normal saline and a vasoconstrictor epinephrine, a lipoaspirate of 300 cc is recovered (retrieved) within the syringe. The lipoaspirate is processed immediately according to established methods, washed extensively in phosphate buffered saline (PBS) solution and digested with 0.075% collagenase. The enzyme activity is neutralized with Dulbecco's modified eagle medium (DMEM) containing 10% FBS (fetal bovine serum) and, following a centrifugation at 1200 G for 10 minutes, a high density cellular pellet is obtained. Following filtration through an appropriately tight Nylon mesh in order to remove cellular debris, the cells are then ready to be injected into the area of concern in the patient's body or further processed and incubated overnight in a control medium of DMEM, FBS, containing an antibiotic, antimycotic solution. After the firm attachment of the stem cells to the plate, they are washed extensively with PBS solution to remove residual non-adherent red blood cells. Further cellular separation is conducted by separation with monoclonal antibodies coated on magnetic beads. Injection of the lipoaspirate is preferably performed as early as possible after an infarction (and re-canalization, where that procedure is performed to open a blocked artery that caused the infarction).

Figure 2:
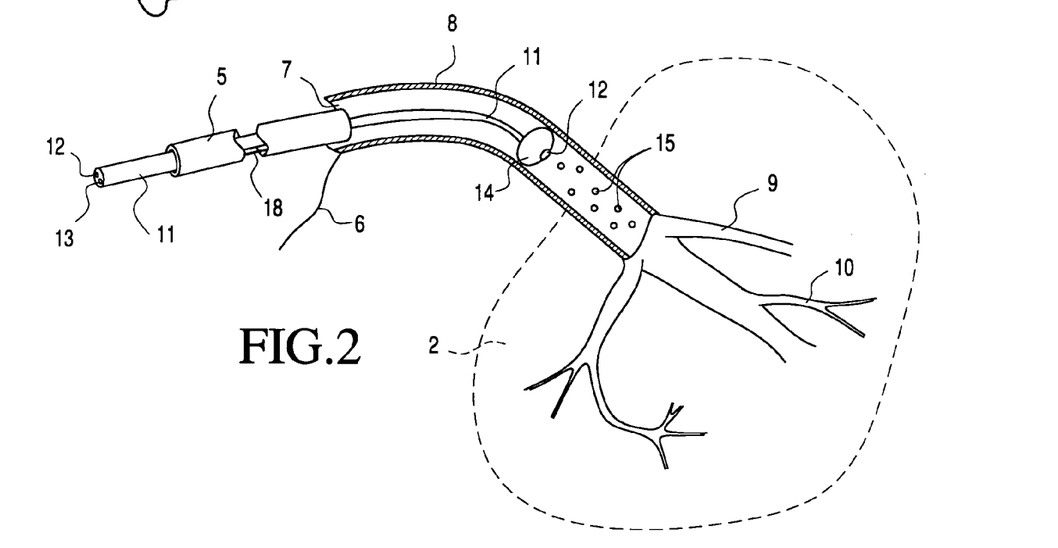
FIG. 2 is a detail view of the injection of cells at the designated site in FIG. 1.

Referring to FIG. 2 as well as to FIG. 1, the recovered autologous adult stem cells are transplanted in the donor patient by intracoronary or transcoronary application for myocardial repair. This process is performed by first introducing a balloon catheter 11 into the cardiovascular system at the patient's groin 3 using an introducer 4, and through a guiding catheter 5 over a guide wire 18 into the aorta 6 and the orifice 7 of a coronary artery 8 of the heart 2 at or in the vicinity of the site where failed tissue owing to an infarction is to be repaired. The failed tissue is supplied with blood through artery 8 and its distal branches 9 and 10. The cells are hand injected or injected through the inner (central) lumen 12 of the balloon catheter 11 by means of a motor driven constant speed injection syringe 16 and connecting catheter 17 to entry point of the central lumen at the proximal end of catheter 11. The exit point of the central lumen 12 is at the distal end of catheter 11 which has been advanced into the coronary artery 8 in proximity to the site of the desired repair. The cells 15 are thereby delivered to this site by means of slow infusion over 15-30 minutes, for example.

A problem encountered in attempting to do this resides in the fact that normally anything inside the blood vessel, including these cells, is separated from the parenchymatous organ or the tissue outside the vessel. In principle, blood flows through the larger arteries into the smaller arteries, into the arterials, into the capillaries, and then into the venous system back into the systemic circulation. Normally, the cells would be prevented from contacting the tissue to be repaired because of the endothelial lining and layer of the vessel that protects the tissue. However, under certain circumstances this barrier is overcome, and the cells can attach to the inside of the vessel, migrate and proliferate in the adjacent tissue. These circumstances are facilitated in the case of situations of acute inflammation such as an acute myocardial infarction, and the increased pressure in the injection system promotes the injected cells to overcome the barrier.

The endothelial ischemic damage owing to the infarction allows white blood cells, especially granulocytes and macrophages, to attach via integrins to the endothelial layer. The endothelial layer itself is dissolved in places by the release of hydrogen peroxide ($H_2O_2$) which originates from the granulocytes. This mechanism produces gaps in the endothelial layer that allow the stem cells to dock to the endothelial integrins and also to migrate through these gaps into the tissue to be repaired. An adjacent factor that enables the stem cells to migrate into the organ tissue is referred to as a stem cell factor that acts as a chemo-attractant to the cells.

One is then still faced with the problems of allowing enough of the repair cells to migrate into contact with the failing tissue and of achieving a high number of transplanted cells in the tissue. This is the principal reason for using a balloon catheter 11 or some other mechanism that will allow the physician (operator) to selectively block the antegrade blood flow and the retrograde stem cell flow. A balloon catheter is preferred because it is a well known, often used and reliable device for introduction to a predetermined site in a vessel such as a coronary artery, to be used for angioplasty for example. In the process of the invention, the balloon 14 of catheter 11 is inflated with biocompatible fluid through a separate lumen 13 of catheter 11 to occlude coronary artery 8 and its distal branches 9 and 10, thereby causing perfusion through the vessel to cease. Inflation of the balloon may be commenced immediately before or at the time of injection of the stem cells through the inner lumen of the catheter, and is maintained throughout the period of injection. This enables the desired large number of adhesions of the cells 15 to the failing tissue to be achieved, because the absence of blood flow at the critical site of this tissue to be repaired has several advantageous effects. It prevents what would otherwise result in a retrograde loss of injected cells, an inability to increase the pressure at the injection site to overcome the endothelial barrier and to force the cells through the gap, and an antegrade dilution with blood flow of the cells being injected to that location through the catheter 11.

Dependent on the type and number of cells delivered, the blockage is maintained for a relatively short period of time, preferably on the order of one to fifteen minutes, and in any event sufficient to allow a high concentration and considerable number of cell attachments to the tissue at the designated site, that will tend to guarantee a successful repair. This repair will extend as well to any failing tissue that may result from the blockage itself. In the case of a slow infusion of the cells, the period of blockage is maintained longer by steady inflation of the balloon over the injection period, say up to about 30 minutes, for enhancement of contact and adherence of abmSC-P to the endothelium. The balloon is deflated, and the balloon catheter is removed from the patient after the procedure.

Previously reported studies have invariably employed a surgical approach for the application of the cells to be transplanted. Even if 5 to 10 sites of injection are performed with small needles, the complete inner, medial and outer layers of the myocardium are never covered. The concept of the present invention to use the natural distribution tree of the arterioles and the capillaries is a more elegant solution, provided that (1) the transplanted cells can overcome the endothelial barrier and migrate into the tissue, (2) interventional cardiology means can restore blood flow into the infarcted area again, and (3) the cells have enough time to overcome the endothelial barrier.

In clinical practice there is a 96% success rate with interventional cardiology to restore blood flow following an acute myocardial infarction after an occlusion of a coronary artery. The experience that venously injected stem cells can be found in the myocardium, and the knowledge that in an acute myocardial infarction the endothelial barrier is considerably damaged (partly due to the $H_2O_2$ release of adhering neutrophilic cells), lead to the conclusion that a local injection into the infarcted area with an occlusive balloon to prevent a washout of the cells is the most desirable approach. The applicant herein has performed studies in the past with a technique called 'BOILER'-lysis, in situations where older venous bypass grafts are occluded by a thrombus that has grown over a prolonged period of time. It was observed that an acute injection of a thrombolytic agent rarely dissolved these old thrombi. But after an over the wire balloon catheter was inserted into the occluded graft, a prolonged application of a thrombolytic substance such as urokinase was successful in achieving thrombolysis. The agent is injected at the tip of the balloon catheter, and is forced antegradely into the thrombus. The inflated balloon prevents a washout by the normal coronary circulation and allows the injection by a motor pump at a defined volume per time. For stem cell therapy and repair as performed by the method of the present invention, an injection over a period of 1 to 30 minutes is feasible and gives the cells sufficient contact time to adhere to the surface of the damaged endothelium.

The invention is not limited to cellular repair of damaged myocardial tissue. Rather, the process by which the repair is performed may be applied to the brain in the case of a patient having suffered a cerebral damage such as an infarction. Previous studied have indicated that stem cells have the capacity to replace neural cells in the brain and therefore overturn the consequences of an acute vascular stroke. In this case, the injection catheter is advanced to the site of the damaged tissue through an appropriate arterial path into the applicable region of the patient's brain, as described more fully below. Blockage of blood flow in this case would add a period (e.g., minutes) of limited blood supply but would enable the cells to overcome the endothelial barrier.

Other possible body organs having damaged tissue to be repaired by the process of the invention include the pancreas, the liver, and the kidneys. The pancreas has a duct (the ductus Wirsungii) through which pancreatic enzymes are delivered into the intestines, and which can be accessed in a retrograde manner by endoscopic retrograde choledocho-pancreaticography (ERCP). Failing tissue in the case of a diabetic patient means that the pancreatic cells therein no longer produce sufficient insulin for the patient's needs. By means of the visual guidance through a small fiberglass instrument a small balloon catheter may be introduced into this duct, and the balloon inflated to occlude the duct during delivery of stem cells through the catheter's inner lumen to the site of the damaged tissue, so as to prevent the injected cells from being washed out into the intestines and thereby enhance large scale adhesions and penetration of the cells to the target tissue.

An analogous procedure is used for repair of damaged tissue of the liver, through the bile duct system. Here also, it is important to overcome the barrier of the normal bile duct with pressure that can be generated only if the balloon is inflated while the cells are slowly injected. The pressure distally of the injection site increases as more and more cells are injected. Repair of failing tissue in the kidney(s) may be repaired by an analogous procedure in the case of a renal infarction.

According to another aspect of the invention, a procedure is used to open up the blood circulation in an ischemic organ and, additionally, to inject stem cells for repair of tissue damage in the organ occasioned by the prior blockage. In a myocardial infarction, for example, only a portion of the myocardial cells that had been ischemic will survive, depending on the time period before which restoration of the blood flow is achieved. A typical procedure is to perform a balloon angioplasty of the blocked artery, followed by implanting a stent at the site of the lesion. But currently, even in the case of optimal treatment some 40% of the affected cells will die. According to this aspect of the invention, within a predetermined brief period after opening the ischemic organ to circulation of blood flow therethrough, autologous adult stem cells are injected into the organ proximate the site of the target tissue for repair thereof. It is imperative that the transplantation of stem cells be performed as soon as possible after re-canalization of the organ, so as to take advantage of the profusion of inflammatory cytokines that accompanies an infarction, which promote the adhesion, migration and proliferation of the stem cells in the tissue. Occlusion of blood flow is desirable here to take advantage of this earlier inflammation.

It should also be noted that while stem cells, particularly autologous adult stem cells, or multipotent cells, are presently preferred for use in the methods of the invention, it is possible that certain modified embryonic stem cells or progenitor cells might be substituted in performing the procedure.

Figures 3, 3A, 3B:
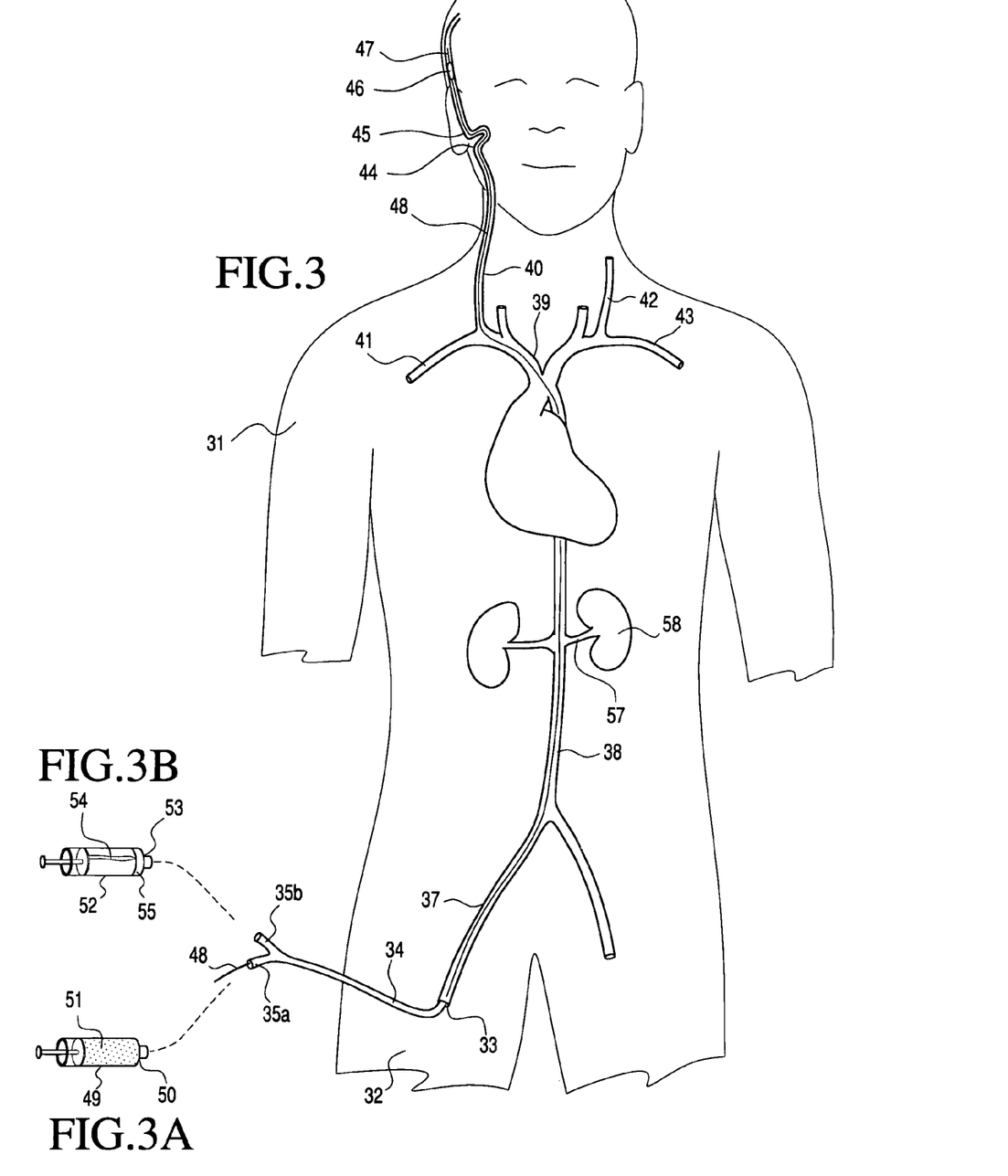
FIG. 3 is a transparent front view of a patient illustrating an exemplary procedure for injecting harvested cells into the cerebral circulation of a patient.
FIGS. 3A and 3B are companion simplified views of syringes used in the course of such a procedure.

FIG. 3 is a diagram useful to describe an example of a method for delivery of stem cells through a balloon-guided catheter to the anterior cerebral circulation in a patient 31.

An introducer sheath 33 of appropriate size, typically 5-7 French, is advanced through the right groin 32. Then a balloon guided double lumen catheter 34 is advanced through introducer sheath 33 and over a small guide wire 48 placed in the artery of interest. Guide wire 48 has a diameter in a range of 0.014 to 0.018 inches, and a flexible distal tip to render it bendable so as to direct the guide wire through the vessel to the vicinity or locality of the selected target site. The proximal end of guide wire 48 is left to project from opening 35a of catheter 34. A side branch opening 35b of catheter 34 is operatively coupled through an inflation lumen of the catheter for selective inflation and deflation of its balloon 46.

Initially, guide wire 48 is advanced through the central lumen of catheter 34. The catheter may then be maneuvered to the selected site by gliding it over the guide wire through iliac artery 37, abdominal and thoracic aorta 38, through the aortic arch 39, and into the right carotid artery 40 beyond the branching off of the vessels 41 for the right arm. As an alternative, guide wire 48 and catheter 34 may be advanced to a location in the left carotid artery 42. The left carotid artery either originates after the branch-off of the left subclavian artery 43, or directly from the aortic arch 39 where the left subclavian artery originates from a separate orifice in the aortic arch.

After advancing guide wire 48 through the common carotid artery into the right internal carotid artery 40 and into the proximal circulation of the Circulus Willisi 44, the anterior cerebral artery 45 is encountered at its origination. After the catheter 34 has been advanced so that its tip 47 and balloon 46 are positioned in the anterior cerebral artery 45, with the catheter tip 47 located at the site to which the harvested autologous adult stem cells are to be delivered, guide wire 48 is removed. The opening 35a of the same lumen that had been used for the guide wire is now available for injecting stem cells for delivery to that site.

Toward that end, and with reference now also to FIGS. 3A and 3B, the conus 50 of a syringe 49 (FIG. 3A) is connected to port 35a of catheter 34, and the conus 53 of another syringe 52 (FIG. 3B) is connected to the inflation port 35b of catheter 34. Port 35b operates through the inflation lumen for balloon 46 of catheter 34. Syringe 52 is of small size and includes a pressure gauge 55 to measure the applied pressure as the fluid 54 within the syringe is expelled into port 35b to inflate balloon 46 to a low pressure of 0.5 to 0.8 atm. This pressure is sufficient to tightly seal the vessel (anterior cerebral artery 45) at the location of the balloon. To assist in recognizing a possible rupture of balloon 46, the fluid 54 in syringe 52 is preferably a 50/50 mixture of saline and contrast dye. Balloon 46 may be deflated at the completion of the procedure or in the event of an emergency by withdrawing the fluid 54 back into syringe 52.

While anterior cerebral artery 45 is tightly sealed toward its proximal end 44, stem cells 51 within syringe 49 are slowly ejected from conus 50 into port 35a of the catheter. The stem cells travel through the central lumen of catheter 34 formerly occupied by guide wire 48 and exit the lumen at the site of catheter tip 47. The stem cells are thus delivered for entry into the cerebral circulation at that site.

As noted earlier herein, the very brief period of limited blood supply during blockage of blood flow through the anterior cerebral artery 45 by inflated balloon 46 is sufficient for the stem cells to overcome the endothelial barrier but not enough to cause injury to the brain.

For treating a diseased or failing kidney, stem cells may be introduced in a similar manner through a catheter navigated over a guide wire in the patient's right groin into the iliac artery 37, the abdominal aorta 38, the applicable renal artery 57, and the diseased kidney 58.

Figure 4:
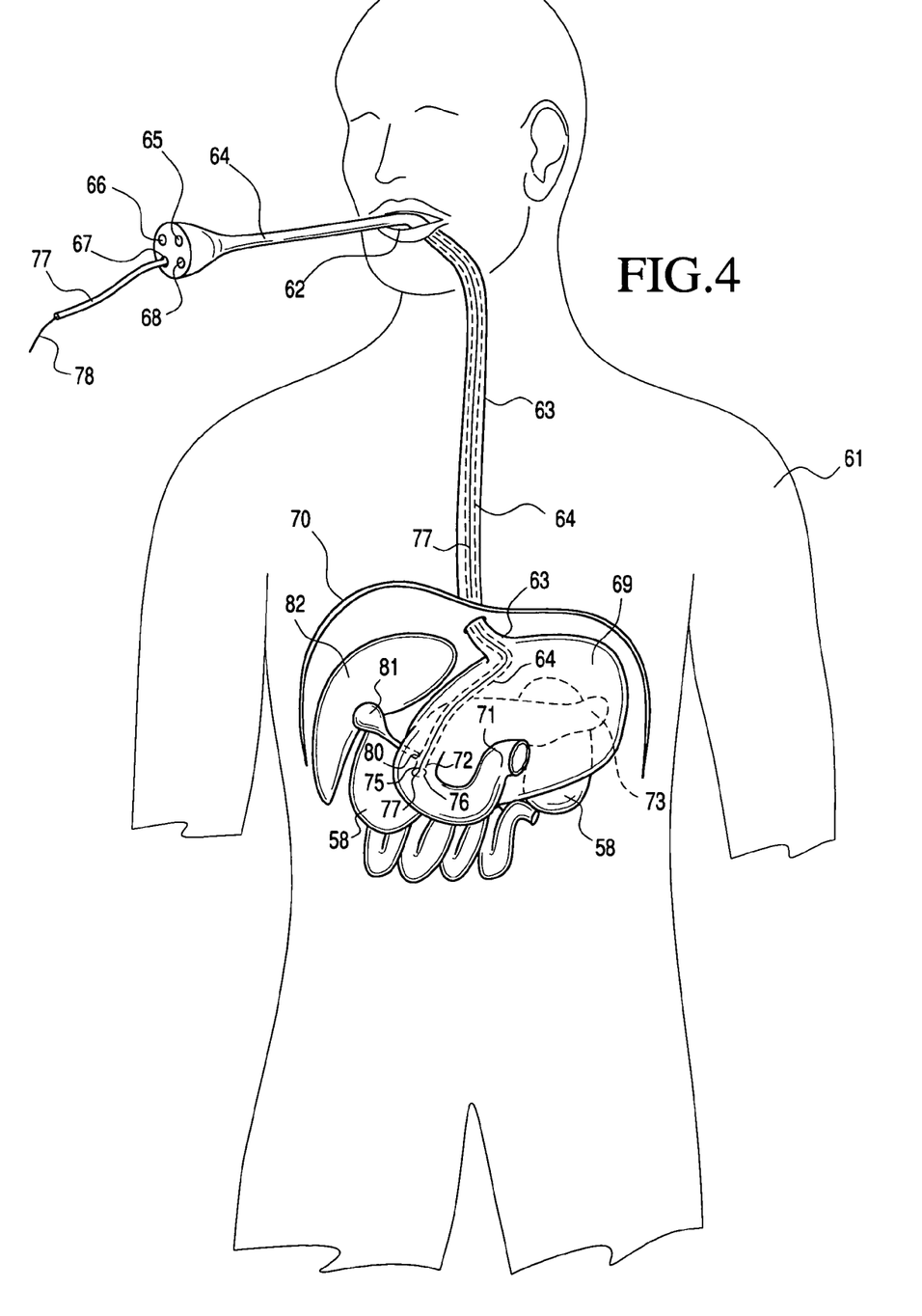
FIG. 4 is a transparent front view of a patient illustrating an exemplary procedure for applying harvested stem cells through a duct of a patient's body, to damaged tissue of an organ such as the pancreas or liver.

FIG. 4 is a diagram useful to describe an example of a method for delivery of stem cells through a natural duct in a patient 61. In this exemplary procedure, an endoscope 64 is advanced through the mouth 62 and esophagus 63 of the patient. The endoscope 64 is flexible, and is designed and implemented with a plurality of channels including, in this illustrative embodiment, a visualization and fiber optics channel 65, flushing channel 66, side port open channel 67, and working channel 68. The distal tip 75 of endoscope 64 is readily bendable to allow the endoscope to be advanced through a tortuous path. During the procedure the patient may be give a local anesthetic to prevent gagging.

The endoscope 64 is advanced from the esophagus 63 through the diaphragm 70, into and through the stomach 69, and further until its distal tip is located in the duodenum 71.

If the pancreas is the organ whose tissue is to be repaired, the location of the distal tip should be such that a side port 72 of the endoscope adjacent its distal tip is aligned for entry into the ductus Wirsungii 76, which supports the internal structure of the pancreas 73 with all its side branches. Proper alignment may be verified through the visualization and fiber optics channel 65 of endoscope 64. Then, a small balloon guided catheter 77 (e.g., 2.7 French outer diameter) is advanced over a guide wire 78 threaded through the side port open channel 67 and out of the side port 72 into the ductus Wirsungii.

Stem cells are delivered and the balloon is inflated by the use of syringes in a method similar to that described with respect to FIGS. 3A and 3B. The distal tip of the catheter is advanced through channel 67 of the endoscope 64 and out of the side port 72 to the site of the pancreatic tissue to be repaired. The catheter's balloon is then inflated through the inflation lumen of the catheter to occlude the Wirsungii duct while stem cells are introduced into the pancreatic tissue through the central lumen of the catheter which is now open following removal of the guide wire. By proper positioning of the catheter's distal tip at the site of the damaged tissue, the cells are delivered into the locale of that site. Occlusion of the duct precludes the stem cells from washing out into the intestines, so as to enhance penetration of the cells to the target tissue and large scale adhesions.

If the patient's liver 82 is the organ whose tissue is to be repaired by delivery of stem cells through a natural duct, the distal tip 75 of endoscope 64 is positioned in the duodenum 71 such that its side port 72 is aligned for entry into the common biliary duct 80, which supports the liver 82 and the gall bladder 81. As an alternative, the side branch of the bile duct may be used. The guide wire and balloon catheter are fed through channel 67 and out of side port 72 of the endoscope, into the duct. The distal tip of the catheter is positioned at the target site of the liver tissue, the guide wire is removed, and the catheter's balloon is inflated to occlude the biliary duct during the introduction of stem cells. The cells are injected through the central lumen of the catheter for adhesion to and engraftment at the failing liver tissue.

Thus, the invention will be seen to include a method for repairing tissue of an organ in a patient's body, which comprises delivering adult stem cells that have the capability to replace tissue of a failing organ to the site of the tissue to be repaired, by an intraluminal application through a blood vessel of the site, and occluding the blood vessel proximal to the location of cell entry therein via the intraluminal application during at least a portion of the duration of the cell delivery to increase the concentration of cells delivered to the target site. The intraluminal application of adult stem cells through the blood vessel may be performed through an arterial vessel or through a venous vessel. Preferably, a balloon catheter is employed for the intraluminal application, and occlusion of the blood vessel is performed by inflating the catheter's balloon for a time interval prescribed to increase the concentration of cells delivered to the target site. The method further includes introducing a guide wire through the blood vessel to the target site, and thereafter advancing the catheter over the guide wire until the distal end of the catheter reaches a selected point in the vicinity of the target site for delivering the adult stem cells.

Autologous adult cells are harvested from the patient's own body, from the bone marrow, from adipose tissue, or from lipoaspirate, as the source of the cells to be delivered to the target site. The harvesting should be performed within a sufficiently short time interval immediately prior to the time the cells are to be delivered, so as to enhance the likelihood of successful organ tissue repair.

It will also be seen from the foregoing description that the invention includes a procedure for repairing tissue of an organ in a patient's body, which comprises delivering adult stem cells that have the capability to replace tissue of a failing organ to the site of the organ tissue to be repaired, by intraluminal application through a duct leading to the target site and normally supporting secretion flow from the organ or a related gland. The intraluminal application includes advancing a catheter through the duct to the vicinity of the target site, and occluding the duct proximal to the location of the intraluminal application during the cell delivery to enhance the concentration of cells delivered to the target site. The intraluminal application is preferably performed in a retrograde manner though the duct.

Here, also, a balloon catheter is used, and occlusion of the duct is performed by inflating the balloon of the catheter for a time interval prescribed to achieve enhancement of cell concentration. The catheter is advanced over a guide wire that has been introduced into the duct, for over-the-wire guidance of the distal end of the catheter along the guide wire to the target site.

The organ whose injured or damaged tissue is to be repaired using an appropriately elected one of these methods may be one among the patient's heart, brain, liver, kidney, pancreas, lungs, nerves, and muscles.

More generally, then, a method has been described herein of delivering adult multipotent cells to a patient's organ through a balloon catheter placed in a vessel or a duct supporting the organ by occluding the vessel or duct at least partially and temporarily during cell delivery proximal to the targeted site of cell delivery for enhanced engraftment of the cells applied to the specific organ.

Although a presently contemplated best mode and alternative modes of practicing the invention has been disclosed by reference to certain preferred methods, it will be apparent to those skilled in the art from a consideration of the foregoing description that variations and modifications may be made without departing from the spirit and scope of the invention. Accordingly, it is intended that the invention shall be limited only by the appended claims and the rules and principles of applicable law.

What is claimed is:

1. A method for repairing tissue in a patient's heart, comprising:
   delivering adult stem cells that have the capability to replace tissue of a failing heart to the site of the tissue to be repaired, by an intraluminal application through a blood vessel of said site; and
   occluding said blood vessel proximal to the location of cell entry therein via said intraluminal application during at least a portion of the duration of said cell delivery to increase the concentration of cells delivered by the blood vessel, and wherein said blood vessel leads to the site of the heart tissue to be repaired.

2. The method of claim 1, wherein the intraluminal application of adult stem cells through a blood vessel is performed through an arterial vessel.

3. The method of claim 1, wherein the intraluminal application of adult stem cells through a blood vessel is performed through a venous vessel.

4. The method of claim 1, including employing a balloon catheter for said intraluminal application, and performing said occlusion of the blood vessel by inflating the balloon of said catheter for a time interval prescribed to increase the concentration of cells delivered to said site.

5. The method of claim 4, including introducing a guide wire through said blood vessel to said site, and thereafter advancing said catheter over the guide wire until the distal end of the catheter reaches a selected point in the vicinity of said site for delivering the adult stem cells.

6. The method of claim 1, including harvesting autologous adult cells from the patient's own body as the source of said cells to be delivered to said site.

7. The method of claim 6, including harvesting said autologous adult cells from the patient's bone marrow.

8. The method of claim 6, including harvesting said autologous adult cells from the patient's adipose tissue.

9. The method of claim 1, wherein said cells originate from lipoaspirate.

10. The method of claim 6, including performing said harvesting within a sufficiently short time interval immediately prior to said delivery to enhance the likelihood of successful organ tissue repair.

11. A method of delivering adult multipotent cells to a patient's heart through a balloon catheter placed in a vessel supporting said heart by occluding said vessel at least partially and temporarily during cell delivery proximal to the site of cell delivery for enhanced engraftment of the cells applied to the heart, and wherein the vessel leads to the site of cell delivery.

* * * * *